US00PP10843P

United States Patent [19]

Tamura et al.

[11] Patent Number: Plant 10,843

[45] Date of Patent: Mar. 30, 1999

[54] TORENIA PLANT NAMED 'SUNRENILABU'

[75] Inventors: Yuji Tamura, Yamanashi; Kiyoshi Miyazaki, Kofu, both of Japan

[73] Assignee: Suntory Limited, Osaka, Japan

[21] Appl. No.: 927,082

[22] Filed: Sep. 10, 1997

[30] Foreign Application Priority Data

Sep. 11, 1996 [JP] Japan ..... 9125

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 10,118 11/1997 Miyazaki et al. ..... Plt./68.1

P.P. 10,119 11/1997 Nagase ..... Plt./68.1

P.P. 10,120 11/1997 Nagase ..... Plt./68.1

*Primary Examiner*—Elizabeth Kemmerer

*Attorney, Agent, or Firm*—Burns, Doane, Swecker & Mathis, L.L.P.

[57] ABSTRACT

Disclosed herein is a torenia plant which has large flowers and bi-color flower petals with light purple, deep purple and vivid purple, and light purple floral tube. The plant has semi-erect growth habit, medium branching and great profusion blooms, and the whole bush remains in bloom for a considerable period of time. The plant has a high resistance to heat, moderate resistance to diseases and pests, and grows and has flowers ordinarily in the shade of trees.

2 Drawing Sheets

BACKGROUND OF THE VARIETY

The present invention relates to a new and distinct variety of torenia plant obtained from the mutant of "Sunrenibu" which was obtained from crossing of "Crown Mix" (♀) and "Con Color" (♂).

The torenia is a very popular plant and is used for flower bedding and potting in the summer season. There are only a few varieties of the torenia plant which have a semi-erect growth habit, a high resistance to heat and diseases. And the torenia plant needs full sunshine and hardly grows and has flowers in the shade of trees. Accordingly, this invention was aimed at obtaining a new variety having a great profusion of flowers, very big flower, light purple, deep purple and vivid purple bi-color flower petal with light purple floral tube, semi-erect growth habit, a high resistance to heat and diseases, and growing and having flowers ordinarily in the shade of trees.

The new variety of torenia plant according to this invention originated from the mutant of a spontaneously generic variant of "Sunrenibu" (U.S. Application. Ser. No. 559,853) which we previously filed. The new variety of torenia plant was discovered in view of large diameter flower during propagation of "Sunrenibu" in April, 1995. The discovered torenia plant was propagated by cutting from summer, 1995 and then grown in bed and pot on trial from summer, 1995 at the Hakushu Nursery Center of SUNTORY Ltd., residing at 2913-1 Torihara, Hakushu-cho, Kitakoma-gun, Yamanashi-ken, Japan. The botanical characteristics of the plant was examined, using parent variety, "Sunrenibu" and the similar variety "Crown Violet", for comparison. As a result, it was concluded that this discovered torenia plant is distinguishable from any other variety, whose existence is known to us, sufficiently uniform and stable in its characteristics, then this new variety of torenia plant was named "Sunrenilabu".

In the following description, the color-coding is in accordance with The Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The mutant parent variety "Sunrenibu" of this new variety "Sunrenilabu" is presently planted and maintained at the Hakushu Nursery Center of SUNTORY Ltd., residing at 2913-1 Torihara, Hakushu-cho, Kitakoma-gun, Yamanashi-ken, Japan. The main botanical characteristics of "Sunrenibu" are as follows.

Plant:

*Growth habit.*—Semi-erect. The stems hang down pliantly when potted in a hanging pot.

*Plant height.*—15–20 cm.

*Plant extension.*—50–70 cm. The stem extends to length of 70 cm from the base.

*Growth.*—Medium branching, a great profusion of blooms; the whole bush remaining in bloom for a considerable this period of time.

*Blooming period.*—June to November in the southern Kanto area, Japan. The plant shape does not change throughout this period.

Stem:

*Diameter.*—2.0mm.

*Anthocyanin pigmentation.*—Present.

*Branching.*—Medium.

*Pubescence.*—Few.

*Length of internode.*—4–6 cm.

Leaf:

*Phyllotaxis.*—Opposite.

*Shape of blade.*—Serrate.

*Length.*—1.0–3.0 cm.

*Width.*—1.0–2.0 cm.

*Depth of incision.*—Medium.

*Color.*—Moderate olive green (R.H.S. 137A, JHS 3508).

*Pubescence.*—Few.

Flower:

*Facing direction.*—Laterally.

*Diameter.*—2.0–3.0 cm.

*Height.*—20–30 mm.
*Color of floral tube.*—Light Purple (R.H.S. 92B, JHS 8303).
*Color of petal.*—Single color, Vivid purple (R.H.S. 89B, JHS 8607).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 2.0–3.0 cm in length.
*Reproductive organs.*—1 pistil and 4 stamens.
*Anther color.*—White.
*Flowering duration.*—Medium.

Physiological and ecological characteristics: Medium resistance to diseases and pests, high tolerances to heat and low tolerance to cold. The plant grows and has flowers ordinarily in the shade of trees.

This new variety, "Sunrenibu" of torenia plant is most suitable for flower bedding and potting, particularly in hanging pots or planters.

The similar variety "Crown Violet" of this new variety "Sunrenilabu" is one of the Crown Series bred by the Sakata Seed Corp., Japan. The Crown Series include a plant having purplish blue flower petals, white flower petals, bi-color of white and purplish blue and the like, and these plants are commonly characterized by a high resistance to heat and are on the market in Japan. The main botanical characteristics of "Crown Violet" are as follows.

Plant:
*Growth habit.*—Erect.
*Plant height.*—20–30 cm.
*Plant extension.*—30–50 cm.

Stem:
*Diameter.*—3.0mm.
*Anthocyanin pigmentation.*—Present.
*Branching.*—Few.
*Pubescence.*—Few.
*Length of internode.*—1–3 cm.

Leaf:
*Phyllotaxis.*—Opposite.
*Shape of blade.*—Serrate.
*Length.*—2.0–4.0 cm.
*Width.*—2.0–3.0 cm.
*Depth of incision.*—Deep.
*Color.*—Moderate olive green (R.H.S. 137A, JHS 3508).
*Pubescence.*—Few.

Flower:
*Facing direction.*—Laterally.
*Diameter.*—2.0–3.0 cm.
*Height.*—20–30 mm.
*Color of floral tube.*—Soft violet (R.H.S. 92C, JHS 8008).
*Color of petal.*—Single color; purplish white (R.H.S. 62D, JHS 8001).
*Yellow eye color.*—Present. Vivid yellow (R.H.S. 17C, JHS 2507).
*Calyx.*—1.5–2.0 cm in length.
*Anthocyanin pigmentation of calyx limb.*—Present.
*Peduncle.*—1.5–2.0 mm in thickness; and 1.5–2.0 cm in length.
*Reproductive organs.*—1 pistil and 4 stamens.
*Anther color.*—White.
*Flowering duration.*—Medium.

Physiological and ecological characteristics: Low resistance to diseases and pests, high tolerances to heat and low tolerance to cold.

"Con Color" used as the male parent in the crossing of "Sunrenibu", which is this new variety mutant parent, is one of the Con Color Series bred by the Sakata Seed Corp., Japan. The Con Color Series include a plant having violet flower petal, bi-color of storing purple and Pale purple and the like, and these plants are commonly characterized by a high resistance to heat and are on the market in Japan. The main botanical characteristics of "Con Color" are as follows.

Plant:
*Growth habit.*—Decumbent.
*Plant height.*—10–15 cm.
*Plant extension.*—50–70 cm.

Stem:
*Diameter.*—1.5 mm.
*Anthocyanin pigmentation.*—Present.
*Branching.*—Many.
*Pubescence.*—Few.
*Length of internode.*—4–6 cm.

Leaf:
*Phyllotaxis.*—Opposite.
*Shape of blade.*—Crenate.
*Length.*—1.0–2.0 cm.
*Width.*—1.0–2.0 cm.
*Depth of incision.*—Medium.
*Color.*—Moderate olive green (R.H.S. 137A, JHS 3508).
*Pubescence.*—Few.

Flower:
*Facing direction.*—Laterally.
*Diameter.*—2.0–3.0 cm.
*Height.*—20–30 mm.
*Color of floral tube.*—Moderate Purple (R.H.S. 83B, JHS 8613).
*Color of petal.*—Single color, Deep purple (R.H.S. 89C, JHS 8311).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 3.0–5.0 cm in length.
*Reproductive organs.*—1 pistil and 4 stamens.
*Anther color.*—White.
*Flowering duration.*—Medium.

Physiological and ecological characteristics: High resistance to diseases and pests, high tolerances to heat and low tolerance of cold.

SUMMARY OF THE VARIETY

The new variety of torenia plant has large flowers and bi-color flower petals with light purple, deep purple and vivid purple, and light purple floral tube, and thus is very different from a similar variety, "Crown Violet", "Sunrenibu" and "Con Color". The plant has semi-erect habit, medium branching and great profusion blooms, and the whole bush remains in bloom for a considerable period of time. The plant has a high resistance to heat, moderate resistance to diseases and pests, and grows and has flowers ordinarily in the shade of trees.

DESCRIPTION OF THE VARIETY

Figure 1:
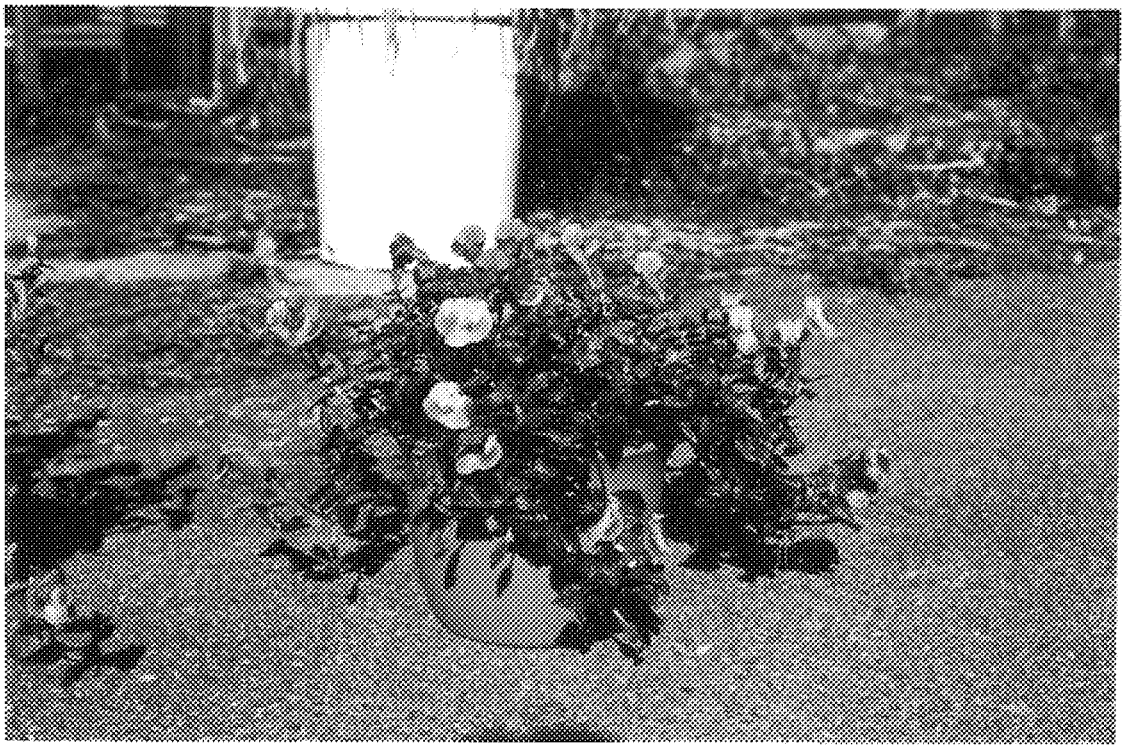
FIG. 1 is a photograph giving a partial view of the new variety of torenia plant planted in a flower pot.
Figure 2:
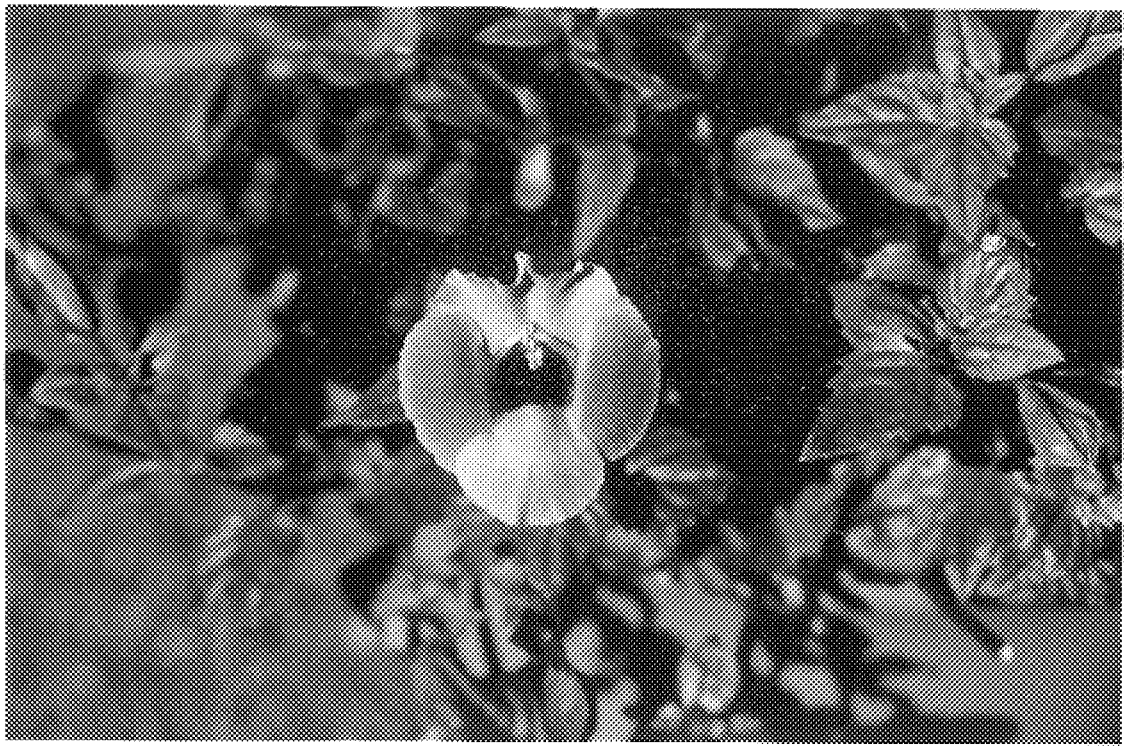
FIG. 2 is a photograph of flowers of the new variety of torenia plant.

The botanical characteristics of the new and distinct variety of torenia plant "Sunrenilabu" are as follows.

Plant:

*Growth habit.*—Semi-erect. The stems hang down pliantly when potted in a hanging pot.

*Plant height.*—15–20 cm.

*Plant extension.*—60–80 cm. The stem extends to length of 80 cm from the base.

*Growth.*—Medium branching, a great profusion of blooms; the whole bush remaining in bloom for a considerable this period of time.

*Blooming period.*—June to November in the southern Kanto area, Japan. The plant shape does not change throughout this period.

Stem:

*Diameter.*—1.5–2.0 mm.

*Anthocyanin pigmentation.*—Present.

*Branching.*—Medium.

*Pubescence.*—Few.

*Length of internode.*—5–7 cm.

Leaf:

*Phyllotaxis.*—Opposite.

*Shape of blade.*—Serrate.

*Length.*—2.5–3.5 cm.

*Width.*—2.0–3.0 cm.

*Depth of incision.*—Medium.

*Color.*—Moderate olive green (R.H.S. 137A, JHS 3508).

*Pubescence.*—Few.

Flower:

*Facing direction.*—Laterally.

*Diameter.*—3.0–4.0 cm.

*Height.*—20–30 mm.

*Color of floral tube.*—Light purple (R.H.S. 85A, JHS 8303).

*Color of petal.*—Bi color,Upper petal : Light purple (R.H.S. 85A, JHS 8303), Lower petal : deep purple (R.H.S. 84A, JHS 8305), Light and left petal : vivid purple (R.H.S. 87A, JHS 8306).

*Yellow eye color.*—Absent.

*Calyx.*—2.0–2.5 cm in length.

*Anthocyanin pigmentation of calyx limb.*—Present.

*Peduncle.*—2.0–3.0 mm in thickness; and 2.0–3.0 cm in length.

*Reproductive organs.*—1 pistil and 4 stamens.

*Anther color.*—White.

*Flowering duration.*—Medium.

Physiological and ecological characteristics: Medium resistance to diseases and pests, high tolerances to heat and low tolerance to cold. The plant grows and has flowers ordinarily in the shade of trees.

This new variety "Sunrenilabu" of torenia plant is most suitable for flower bedding and potting, particularly in hanging pots or planters.

The plant of this new variety "Sunreilabu" is presently planted and maintained at the Hakushu Nursery Center of SUNTORY Ltd., residing at 2913-1 Torihara, Hakushu-cho, Kitakoma-gun, Yamanashi-ken, Japan.

We claim:

1. A new and distinct variety of torenia plant, substantially as herein illustrated and described, characterized particularly as to novelty by (A) having large flowers and bi-color flower petals with light purple, deep purple and vivid purple, and light purple floral tube, (B) semi-erect growth habit, medium branching and great profusion blooms, the whole bush remaining in bloom for a considerable period of time, (C) a high resistance to heat, moderate resistance to diseases and pests and (D) growing and having flowers ordinarily in the shade of trees.

* * * * *